(12) United States Patent
Mancuso

(10) Patent No.: US 8,157,791 B2
(45) Date of Patent: Apr. 17, 2012

(54) SYSTEM AND METHOD FOR POST-OPERATIVE CARE FOR A LIPOSUCTION PROCEDURE

(76) Inventor: Gwen Mancuso, San Francisco, CA (US)

( * ) Notice: Subject to any disclaimer, the term of this patent is extended or adjusted under 35 U.S.C. 154(b) by 456 days.

(21) Appl. No.: 12/499,640

(22) Filed: Jul. 8, 2009

(65) Prior Publication Data

US 2011/0009845 A1 Jan. 13, 2011

(51) Int. Cl.
*A61F 13/15* (2006.01)
(52) U.S. Cl. .................. 604/542; 604/385.12; 604/378; 604/385.03; 604/391; 604/397
(58) Field of Classification Search .................. 604/542, 604/385.12, 378, 385.03, 391, 397
See application file for complete search history.

(56) References Cited

U.S. PATENT DOCUMENTS

| 6,269,820 B1 * | 8/2001 | Bays | 128/898 |
| 2010/0082007 A1 * | 4/2010 | Bobo | 604/385.03 |

* cited by examiner

*Primary Examiner* — Jacqueline F. Stephens

(57) ABSTRACT

A system and method for post-operation care for a liposuction procedure including a compression garment and a set of absorptive garments that includes a first absorptive garment and a second absorptive garment. The compression garment includes a first portion and each absorptive garment includes an absorptive material, a fluid resistant material, and a fastener. The first absorptive garment is coupled to the body of the patient and fastened to envelop the first portion of the absorptive garment and the second absorptive garment is couple to the body of the patient and fastened to the first portion of the absorptive garment upon removal of the first absorptive garment.

18 Claims, 4 Drawing Sheets

SYSTEM AND METHOD FOR POST-OPERATIVE CARE FOR A LIPOSUCTION PROCEDURE

TECHNICAL FIELD

This invention relates generally post-operative patient care for a liposuction procedure, and more specifically, a system to ease the recovery process for the patient and to facilitate the containment of fluids excreted by the patient through the operation incision locations.

BACKGROUND

Liposuction is currently the most popular operation in the field of cosmetic surgery. Every year, about 500,000 liposuction operations are performed in the United States. Several techniques exist to perform the liposuction procedure including dry liposuction and wet liposuction. Wet liposuction, which is the most common procedure, has the advantages of decreasing the bleeding, the bruising, and the need for general anesthetic. The procedure, however, requires the injection of a fluid into the liposuction area. The fluid may then be left inside the body to be reabsorbed by the patient's lymphatic system, but may alternatively be allowed to exit the patient's body over a period of several days post-operation through the incision locations. The exit of the post-liposuction fluid through the incision locations may be preferred because of decreased recovery time and lower chance of the formation of minor complications such as seronoma formation.

During typical post-liposuction recovery, the patient is generally recommended by the physician to wear a compression garment continuously. The compression garment functions to apply pressure around a liposuction area, facilitating the exit of the post-liposuction fluid through the incision location. Because the compression garment is to be worn continuously for several days to several weeks post-operation, the compression garment is generally of an air and fluid permeable elastic material such as nylon to allow the skin of the patient to breathe and to heal and sweat to permeate through the garment. As a result, the post-liposuction fluid exits the patient's body and permeates through the compression garment in an uncontrolled fashion. This may lead to difficulties for the patient as the post-liposuction fluid is excreted uncontrollably and may seep into their clothing, bed, etc, in an undesirable manner. Patients may place absorptive pads inside their compression garment to capture the post-liposuction fluid, but this decreases the breathability of the compression garment and requires the user to remove the compression garment to replace a soiled absorptive pad, causing both an inconvenience and the interruption of the recommended constant pressure on the liposuction area. This invention provides a system and a method to be used post-liposuction to facilitate the capture of the exiting post-liposuction fluid while maintaining the breathability of the compression garment and facilitating the recovery process for the patient.

DESCRIPTION OF THE PREFERRED EMBODIMENTS

The following description the preferred embodiments of the invention is not intended to limit the invention to these preferred embodiments, but rather to enable any person skilled in the art to make and use this invention.

Figure 2:
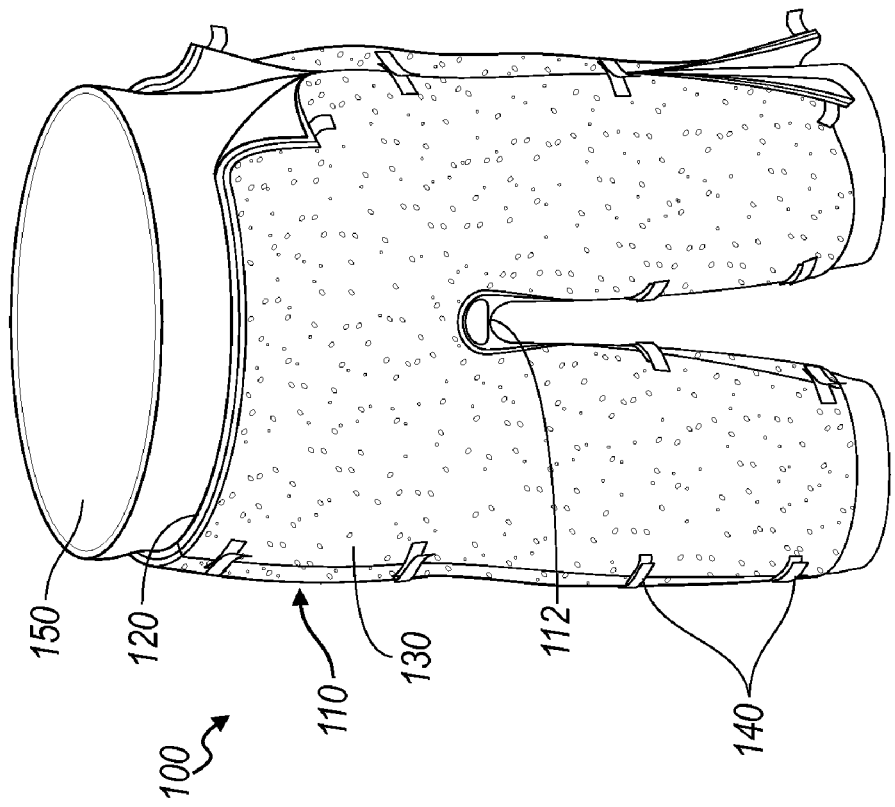
FIG. 2 is a schematic representation of the system of the preferred embodiments, including an absorptive garment and a compression garment.
Figure 1:
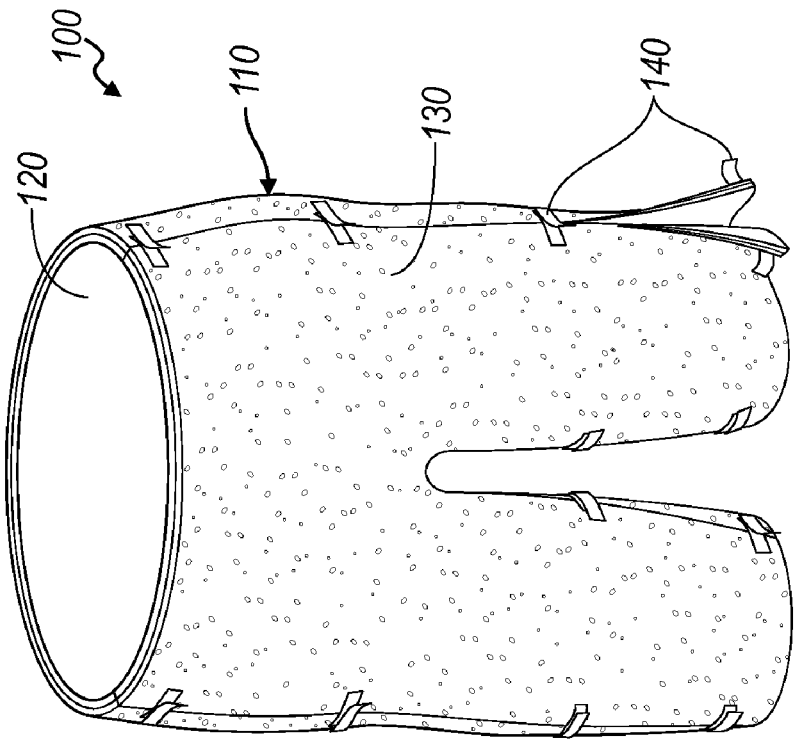
FIG. 1 is a schematic representation of the absorptive garment of the preferred embodiments.

As shown in FIG. 1, the system 100 of the preferred embodiments includes an absorptive garment 110 that functions to absorb and contain the post-liposuction fluid that exits from the patient's body. The absorptive garment 110 includes an absorptive material 120 that captures a substantial portion of the volume of post-liposuction fluid, a fluid resistant material 130 that is air permeable, and a fastener 140 that couples the absorptive garment to the patient and arranges the absorptive garment 110 at a position relative to the body of the patient. As shown in FIG. 2, the system 100 may also include a compression garment 150 that applies pressure to the liposuction area on the body of the patient and allows the permeation of post-liposuction fluids. The absorptive garment 110 may be separately used by the user, but is preferably used with the compression garment 150 that provides the compressive force that facilitates the exit of the post-liposuction fluid from the incision location. When used with the compression garment 150, the absorptive garment 110 is preferably placed over the compression garment 150 and easily removed and replaced when soiled or at any other suitable time. The absorptive garment 110 may be provided to the patient as an individual component, but may alternatively be provided to the user as a part of a post-operative care kit that includes the absorptive garment 110 and the compression garment 150. The kit may include a series of absorptive garments 110 with a single compression garment 150, a series of absorptive garments 110 and a series of compression garments 150, or any other suitable combination of absorptive garments 110 and compression garments 150.

Figure 3:
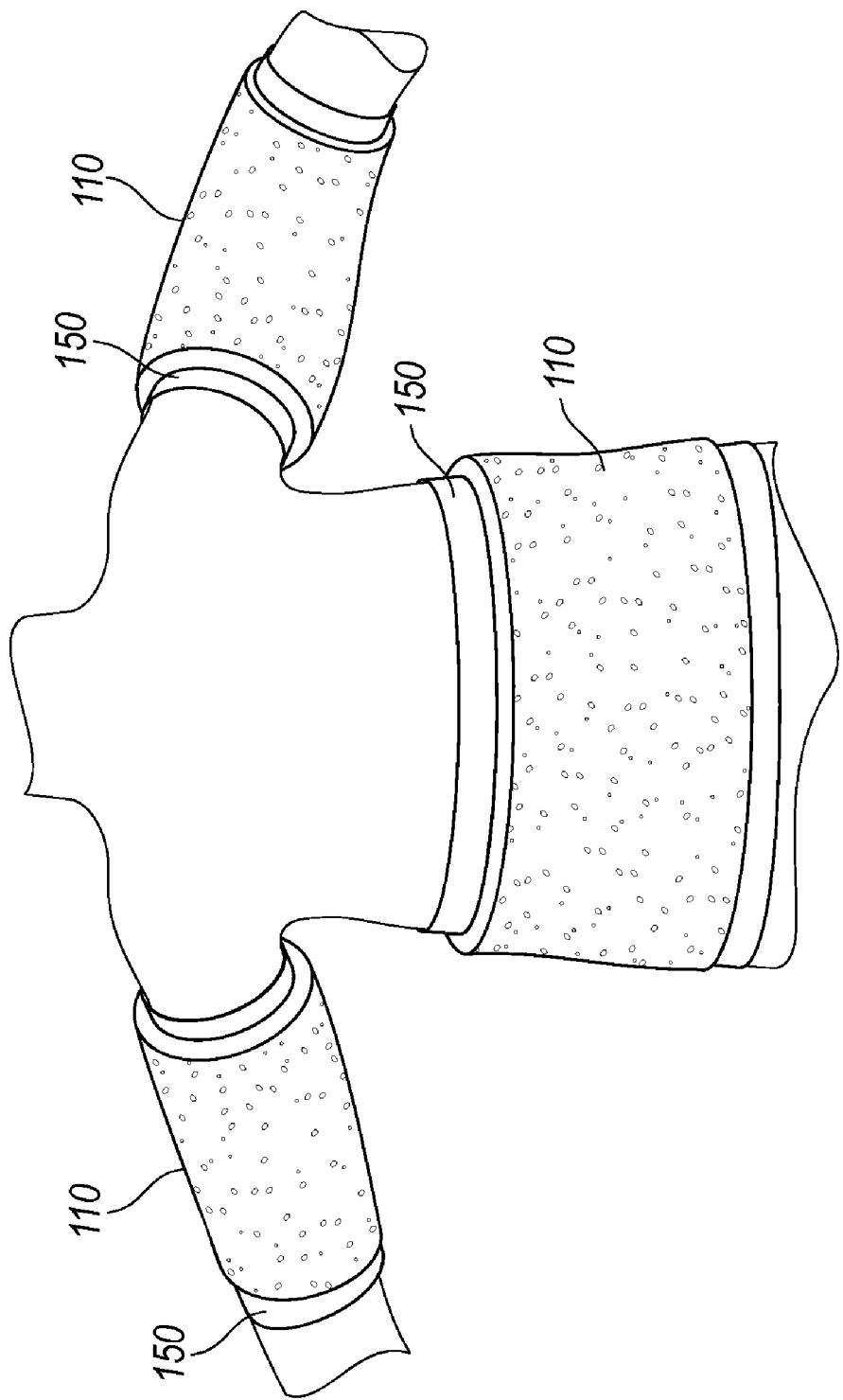
FIG. 3 is a schematic representation of the system of the preferred embodiments, in alternative orientations and arrangements.

The absorptive garment 110 preferably functions to envelop a portion of the body that includes the liposuction area. In the variation of the system 100 that includes the compression garment 150, the absorptive garment 110 preferably functions to envelop a first portion of the compression garment 150. The system 100 may also include a second absorptive garment that functions to envelop a second portion of the body that may include a second liposuction area or a second incision location or may function to envelop a second portion of the compression garment 150. The first and/or second portion of the compression garment 150 is preferably located at a region on the body that includes the incision location for the liposuction procedure. The first portion of the compression 150 may also include a substantial portion of the total surface area of the compression garment 150. As shown in FIGS. 1-3, the absorptive garment 110 and the compression garment 150 preferably include geometry that allows the absorptive garment 110 and the compression garment 150 to accommodate to the portion of the body of the patient that includes the liposuction area and the incision location for the liposuction procedure. The components of the absorptive garment 110 and the compression garment 150 may be cut and assembled to contain the geometry, but the absorptive garment 110 may also be sewn, fastened, or glued to create the geometry. However, any other suitable method to create the geometry may be used. Common areas that are targeted for liposuction procedures include the abdomen, hip, thigh, buttocks, and arms. As shown in FIGS. 1 and 2, the absorptive garment 110 includes geometry to allow the absorptive garment 110 to accommodate to the thighs, hip, and crotch area of the body. In the variation of the absorptive garment 110 that includes geometry to allow the accommodation to the crotch area of the body, the absorptive garment 110 preferably defines an aperture 112 to allow the passage of patient waste such as urine and fecal waste to allow the patient to relieve himself or herself without removal of the absorptive garment 110. The compression garment 150 in this variation also preferably includes a similar aperture to allow the passage of patient waste to allow the patient to relieve himself or herself without removal of the compression garment 150. By including geometry that allows the absorptive garment 110 to accommodate to a specific portion of the body, excessive material is decreased, specific areas wherein absorption of post-liposuction fluid is most useful are better targeted, and comfort to the patient is increased. For example, if a combination of square absorptive pads of the prior art were instead to be used in the thighs, hip, and crotch area, there may be overlapping of excessive absorptive material, causing material to bunch up against the patient's body and causing discomfort. The square absorptive pads may also shift and allow gaps in areas where absorption is desired, allowing the post-liposuction fluid to escape the system in an uncontrolled fashion. In addition, the geometry preferably facilitates in arranging the absorptive garment in the desired location. For example, as shown in FIGS. 1 and 2, the geometry to accommodate to the crotch area of the patient facilitates both the patient and the absorptive garment 110 itself to correctly arrange and self-arrange the absorptive garment 110 to the correct placement relative to the patient's body. The fastener 140 may also assist in arranging the absorptive garment 110 in the correct placement while coupling the absorptive garment 110 to the body of the patient. By including geometry that allows the compression garment 150 to accommodate to a specific region of the body, compression is provided substantially evenly to regions of the body that are in contact with the compression garment 150.

The absorptive material 120 is preferably of a material with high absorbency such as high absorbency polymers, allowing the absorptive garment 110 to be relatively thin overall while absorbing and capturing a substantial volume of the post-liposuction fluid. The absorptive material preferably includes a first face that faces the body of the patient and a second face that faces and is coupled to the fluid resistant material 130. In the variation of the system 100 that includes the compression garment 150, the first face of the absorptive material preferably faces the compression garment. The second face is preferably opposite of the first face, and is preferably substantially larger than the remaining faces of the absorptive material 120 to provide a larger surface area to contact the body of the patient. The absorptive material 120 is preferably of uniform thickness to provide even absorptiveness to the portion of the body that the absorptive material 120 is in contact with, but may alternatively be of a non-uniform thickness to potentially provide additional absorptiveness to a particular region of the portion of the body that the absorptive material 120 is in contact with.

The first face of the absorptive material 120 is preferably of a surface area that is substantially identical to the surface area of the portion of the body that contains the liposuction area. In the variation of the system 100 that includes the compression garment 150, the absorptive material 120 is preferably of a surface area substantially identical to the surface area of the compression garment 150. The first face of the absorptive material 120 may alternatively be of a surface area that is smaller than the surface area of the portion of the body that contains the liposuction area or the surface area of the compression garment 150. In this variation, the absorptive material 120 is preferably arranged at a location that includes the incision location to provide absorptiveness to the area where the post-liposuction fluid may exit from the patient. However, any other suitable surface area for the first face of the absorptive material 120 may be used.

The fluid resistant material 130 preferably functions to prevent liquid that has been captured by the absorptive material 120 from escape from the absorptive material 120. The fluid resistant material 130 is preferably also air permeable to allow the skin of the patient to breathe and sweat to evaporate. The fluid resistant material 130 is preferably of a material that substantially prevents the permeation of fluid such as a thin piece of pliable plastic glued or annealed to the second face of the absorptive material 120, a coating applied to the second face of the absorptive material 120 that functions to seal the absorptive material 120, or any other suitable material or method.

The absorptive garment 110 may include a second fluid resistant material that is coupled to the first face of the absorptive material 110. In this variation, the second fluid resistant material functions to allow fluid from the body of the patient to permeate through to the absorptive material, but to discourage fluid that has been captured by the absorptive material to permeate back through to the body of the patient. The second fluid resistant material is preferably of a material that facilitates fluid permeation in one direction and discourages fluid permeation in the opposite direction, such as porous netting that contains geometry to funnel fluid in one direction and to block fluid in the opposite direction.

Figure 4A:
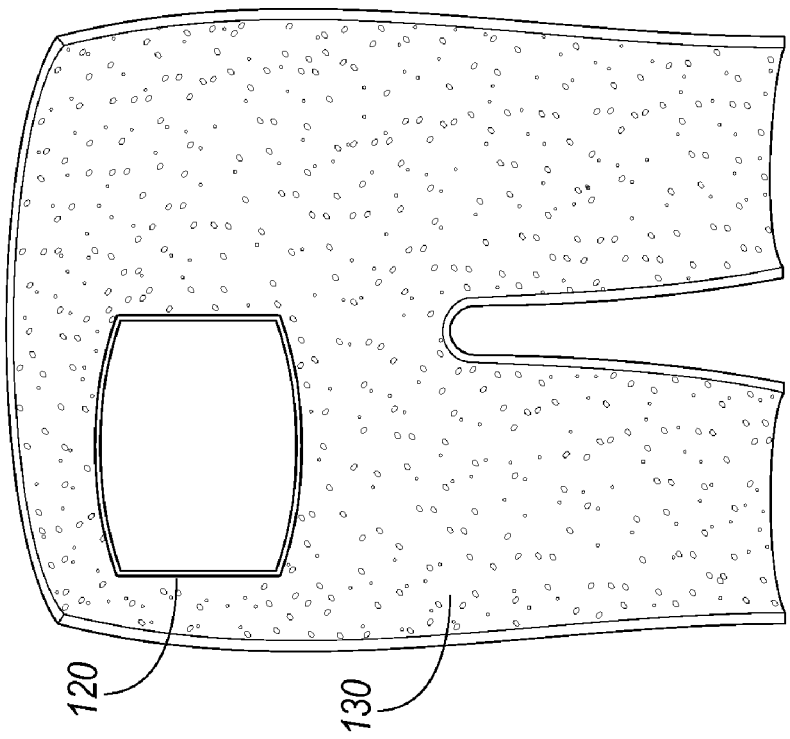
FIGS. 4a and 4b are schematic representations of variations in relative area of the absorptive material and the fluid resistant material of the absorptive garment of the preferred embodiments.
Figure 4B:
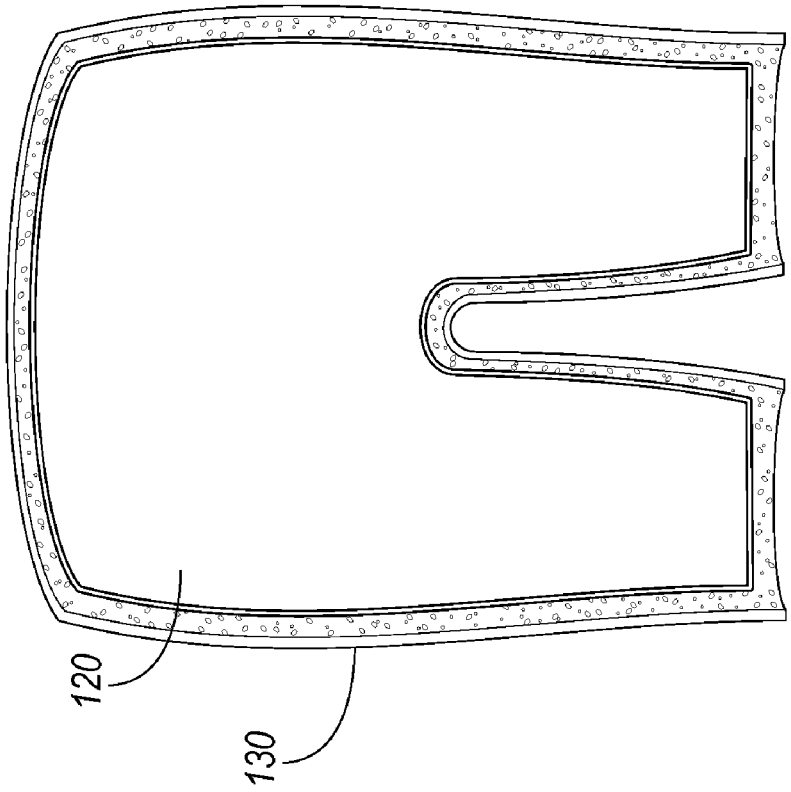

As shown in FIGS. 4a and 4b, the fluid resistant material 130 is preferably of a surface area substantially identical to the surface area of the second face of the absorptive material 120, but may alternatively be of a surface area larger than the surface area of the second face of the absorptive material 120. The fluid resistant material 130 is preferably of a surface area substantially identical to the surface area of the portion of the body that contains the liposuction area. In the variation of the system 100 that includes the compression garment 150, the fluid resistant material 130 is preferably of a surface area substantially identical to the surface area of the compression garment 150. Alternatively, the surface area of the fluid resistant material 130 may be smaller than the surface area of the surface area of the portion of the body that contains the liposuction area or the surface area of the compression garment 150. However, any other suitable surface area for the fluid resistant material 130 may be used.

The fastener 140 preferably functions to couple the absorptive garment 110 to the patient and to arrange the absorptive garment to envelop the portion of the body including the liposuction area or to envelop the first portion of the compression garment 150. The fastener 140 is preferably adjustable to accommodate to a variety of patient sizes. The fastener 140 may utilize the geometry of the absorptive garment 110 to maintain the desired arrangement between the absorptive garment 110 and the body and/or the compression garment 150. For example, in the variation wherein the absorptive garment 110 is to accommodate to the thigh, hip, and crotch area as shown in FIGS. 1 and 2, the absorptive garment 110 preferably wraps around the thighs similar to a pair of pants and prevents rotation of the absorptive garment 110 around the patient. The fastener 140 preferably includes a first component that is mounted at a first location of the fluid resistant material and a second component that is mounted at a second location of the fluid resistant material. The first and second components are then preferably selectively fastened to each other and thus coupling the absorptive garment 110 to the body of the patient and arranging the absorptive garment 110 to envelop a portion of the body including the liposuction area or to envelop the first portion of the compression garment 150. As shown in FIGS. 1 and 2, the first and second components of the fastener 140 are preferably strings that each has a first end sewn to the fluid resistant material 130 and a second end that is free. The free ends of the two strings can be tied to each other. The tying of two free ends of strings allows the fastener 140 to accommodate to a variety of sizes of patients. Alternatively, the first and second components of the fastener 140 may be mating components of Velcro, tape, or any other suitable non-permanent fastener. In the variation wherein the first and second components of the fastener 140 are the mating components of Velcro, the first component may be a first length of the first component of Velcro and the second component may be of a second length of the second component of Velcro, wherein the second length is shorter than the first length. The second component of Velcro may then be coupled to the location along the length of the first component that best accommodates to the size of the patient. However, any other suitable fastener may be used.

The fastener 140 is preferably of a type that does not fully seal the absorptive garment 110 around the body of the user. One of the more important aspects of successful recovery is to allow the incision wound and the skin to breathe and dry, otherwise, the chance for infection or other recovery complications is increased. The fastener 140 preferably functions to couple the first portion and the second portion of the fluid resistant material 130 to each other while allowing fluids (such as air, post-liposuction fluid not captured by the absorptive material 120, or sweat) to pass through the interface between the first location and the second location of the fluid resistant material 130.

Figure 5:
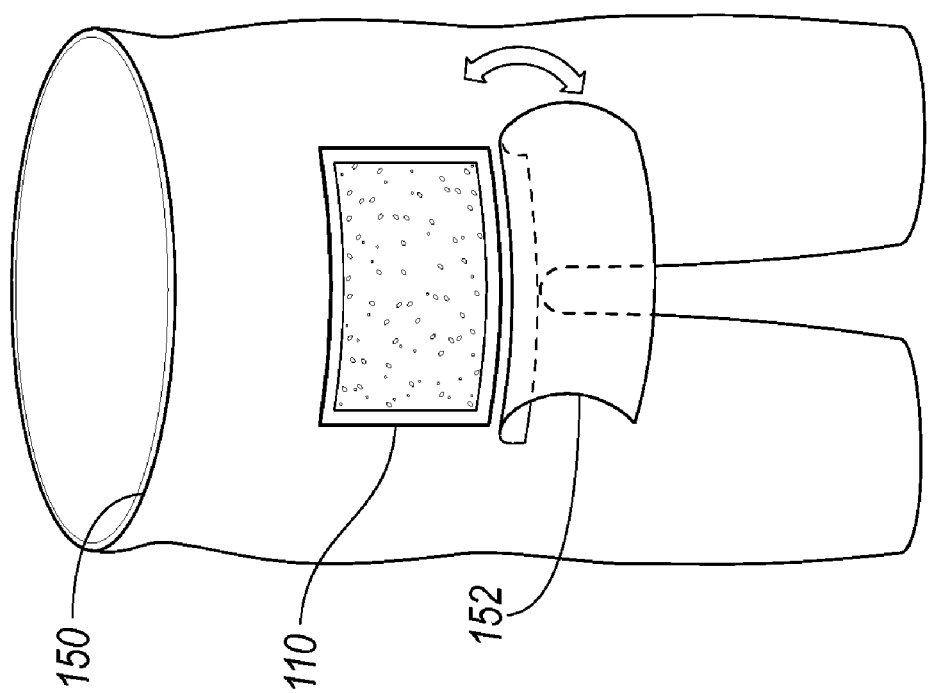
FIG. 5 is a schematic representation of a variation of the absorptive garment and the compression garment of the preferred embodiments.

The compression garment 150 is preferably an elastic material that allows the permeation of fluids (such as air, post-liposuction fluid, and sweat) such as nylon or any other suitable type of material. The elasticity of the material is preferably uniform throughout the material to provide uniform compressive force to the body of the user to facilitate the recovery process. The compression garment 150 may include a first layer and a second layer and the absorptive garment 110 is placed in between the first and second layers. The first layer preferably remains relatively stationary relative to the body of the patient while the second layer may be removed to allow replacement of the absorptive garment 110. This allows the compression garment 150 to maintain compressive force on the body of the patient during the replacement of the absorptive garment 110. In this variation, the second layer of the compression garment 150 may function as the fastener 140. The second layer of the compression garment 150 may include a first portion that remains attached to the first layer during the replacement of the absorptive garment while a second portion is moved relative to the first layer, for example, a flap 152 as shown in FIG. 5. The second layer of this variation is then reattached to the first layer after the absorptive garment 110 is replaced to secure the absorptive garment 110. However, any other arrangement of the compression garment 150 may be used.

As mentioned above, the absorptive garment 110 may be provided to the patient as an individual component, but may alternatively be provided to the user as a part of a post-operative care kit that includes the absorptive garment 110 and the compression garment 150. In a first example of a usage scenario, the user purchases or is provided compression garment 150 and a set of absorptive garments 110. The user then wears the compression garment 150 over the liposuction area and attaches a first absorptive garment 110 over the compression garment 150 using the fasteners 140. The patient adjusts the fasteners 140 until the absorptive garment 110 is arranged comfortably and in the correct orientation. The absorptive garment 110 is preferably relatively loosely attached to the body to allow for ample breathability through the absorptive garment 110 and the compression garment 150 to the skin. When the first absorptive garment 110 becomes soiled or is worn for a period of time, the patient removes the first absorptive garment 110 and preferably discards the first absorptive garment 110 and wears a second absorptive garment 110 in a manner similar or identical to the manner in which the first absorptive garment 110 was worn. The patient may be instructed to wear the compression garment 150 for 3 to 4 days or for several weeks. The patient is preferably provided with a number of absorptive garments 110 that is substantially equal to the number of days the compression garment 150 is to be worn, allowing the user to exchange a soiled absorptive garment 110 for a fresh absorptive garment 110 every day during the recovery period. The patient may be provided with a number of absorptive garments 110 that is larger than the number of days the compression garment 150 is worn to allow the patient to change absorptive garments 110 more than once a day if an absorptive garment 110 becomes soiled. Alternatively, the number of absorptive garments 110 may be less than the number of days the compression garment 150 is to be worn if the volume of post-liposuction fluid that is excreted is not expected to be of a significant level every day during the recovery period. The kit may also include more than one compression garment 150 in preparation for a first compression garment 150 becoming too soiled or not providing enough compressive force. In a second example of a usage scenario, the absorptive garment 110 may be provided separately from the compression garment 150. The absorptive garment 110 may be purchased or provided as an extra absorptive garment 110 to be used with an existing system already provided to the user, but may alternatively be purchased or provided to be used without a compression garment 150, for example, if the patient is not recommended to wear a compression garment 150 or is no longer required to wear a compression garment 150 but is still concerned about uncontrolled exit of post-liposuction fluid. However, the system 100 may be applied to any other suitable usage scenario.

As a person skilled in the art will recognize from the previous detailed description and from the figures and claims, modifications and changes can be made to the preferred embodiments of the invention without departing from the scope of this invention defined in the following claims.

I claim:

1. A kit, for post-operation care of a liposuction incision on the body of a patient following a liposuction procedure, the kit comprising:
a compression garment configured to apply pressure to a portion of the body proximal the liposuction incision, the compression garment substantially permeable to a fluid excreted from the incision;

a set of absorptive garments, including a first absorptive garment and a second absorptive garment, each absorptive garment comprising:
an absorptive material defining a first face configured to contact the compression garment and a second face opposite the first face, the absorptive material configured to retain a portion of the fluid that passes through the compression garmet;
a fluid resistant material non-transiently connected to the absorptive material adjacent the second face; and
a fastener configured to selectively couple the absorptive garment to the patient with the absorptive garment substantially enveloping the compression garment; and
wherein the compression garment is configured to remain in place on the portion of the body of the patient while the first absorptive garment, enveloping the compression garment, is replaced with the second absorptive garment.

2. The kit of claim 1, wherein the compression garment defines a tubular portion configured to apply pressure to the body of the patient proximal the incision.

3. The kit of claim 2, wherein the compression garment and the first and second absorptive garments define geometries configured to envelop portions of the body of the patient selected from the group consisting of: the abdomen, the waist, a thigh, the buttocks, and an arm.

4. The kit of claim 2, wherein the compression garment and the first and second absorptive garments define geometries configured to envelop the crotch of the patient, wherein the geometries comprise apertures configured to permit passage of patient waste therethrough.

5. The kit of claim 1, wherein the first absorptive garment and the second absorptive garment are substantially identical.

6. The kit of claim 1, wherein the first face of the absorptive material defines a surface area that is substantially similar to the surface area of the compression garment.

7. The system kit of claim 1, wherein the first face of the absorptive material defines a surface area that is less than the surface area of the compression garment.

8. The kit of claim 1, wherein the fluid resistant material is substantially permeable to air.

9. The kit of claim 1, wherein the fluid resistant material is of a surface area substantially identical to the surface area of the second face of the absorptive material.

10. The kit of claim 1, wherein the fastener includes a first component mounted at a first location on the fluid resistant material and a second component mounted at a second location on the fluid resistant material, the first component and the second component being selectively fastenable to couple the absorptive garment to the patient with the absorptive garment substantially enveloping the compression garment.

11. The kit of claim 10, wherein the fluid resistant material is configured to permit the passage of the fluid through an interface proximal the first and second locations of the fluid resistant material.

12. The kit of claim 10, wherein the first component of the fastener comprises a first string and the second component of the fastener comprises a second string.

13. The kit of claim 10, wherein the first component of the fastener comprises a material defining a plurality of loops and the second component of the fastener comprises a material defining a plurality of hooks configured to capture and hold a portion of the loops of the first component.

14. The kit of claim 10, wherein the first component and the second component of the fastener are sewn to the fluid resistant material.

15. The kit of claim 1, wherein the fastener is configured to accommodate a plurality of patient sizes.

16. The kit of claim 1, wherein the absorptive material and the fluid resistance material are sewn together to form the absorptive garment.

17. A garment, for the absorption of fluids excreted by a patient from an incision following a liposuction procedure, comprising:
an absorptive material defining a geometry and surface area configured to envelope a portion of the body of the patient proximal the incision and comprising a first face configured to face the body of the patient and a second face opposite the first face, the absorptive material configured to capture a portion of the volume of fluid excreted by the patient;
a fluid resistant material that is air permeable and is of a geometry and surface area substantially identical to the geometry and surface area of the absorptive material, wherein at least a portion of the fluid resistant material is coupled to the second face of the absorptive material to substantially prevent the fluid from exiting the absorptive material through the second face; and
a fastener comprising a first component mounted at a first location on the fluid resistant material and a second component mounted at a second location on the fluid resistant material, wherein the first component and the second component are selectively fastenable to couple the garment to the patient with the garment enveloping the portion of the body of the patient containing the incision;
wherein the absorptive material and the fluid resistant material define an aperture configured to permit passage of patient waste therethrough.

18. A garment, for the absorption of fluids excreted by a patient from an incision following a liposuction procedure, the garment comprising:
an absorptive material defining a geometry configured to envelope a portion of the body of the patient proximal the incision and comprising a first face configured to face the body of the patient and a second face opposite the first face, the absorptive material configured to absorb and retain a portion of the fluid excreted by the patient;
a fluid resistant material that is substantially air-permeable and is of a geometry substantially similar to the geometry of the absorptive material, a portion of the fluid resistant material non-transiently connected to the absorptive material adjacent to the second face to prevent the absorbed fluid from seeping out of the absorptive material from the second face; and
a fastener comprising a first component mounted at a first location on the fluid resistant material and a second component mounted at a second location on the fluid resistant material, the first component and the second component being selectively fastenable to couple the garment to the patient with the garment enveloping the portion of the body of the patient.

* * * * *